(12) United States Patent
Schmitt

(10) Patent No.: US 12,226,615 B2
(45) Date of Patent: Feb. 18, 2025

(54) METHOD AND DEVICE FOR THE NEEDLE-FREE INJECTING OF FLUID INTO A SUBSTRATE

(71) Applicant: Conzima GmbH, Wiggensbach (DE)

(72) Inventor: Fritz Schmitt, Rosport (LU)

(73) Assignee: Conzima GmbH, Wiggensbach (DE)

( * ) Notice: Subject to any disclaimer, the term of this patent is extended or adjusted under 35 U.S.C. 154(b) by 433 days.

(21) Appl. No.: 16/762,198

(22) PCT Filed: Nov. 9, 2018

(86) PCT No.: PCT/IB2018/058813
§ 371 (c)(1),
(2) Date: May 7, 2020

(87) PCT Pub. No.: WO2019/092644
PCT Pub. Date: May 16, 2019

(65) Prior Publication Data
US 2020/0353171 A1 Nov. 12, 2020

(30) Foreign Application Priority Data
Nov. 10, 2017 (DE) ..................... 10 2017 126 493.0

(51) Int. Cl.
*A61M 5/30* (2006.01)
*A61M 5/315* (2006.01)
*A61M 5/24* (2006.01)

(52) U.S. Cl.
CPC ...... *A61M 5/3007* (2013.01); *A61M 5/31583* (2013.01); *A61M 2005/2407* (2013.01);
(Continued)

(58) Field of Classification Search
CPC ........ A61M 5/30; A61M 5/3007; A61M 5/24; A61M 2205/19; A61M 2250/00;
(Continued)

(56) References Cited

U.S. PATENT DOCUMENTS 2,653,604 A * 9/1953 Hein, Jr. ............... A61M 5/30
604/68
2,762,370 A * 9/1956 Venditty ................ A61M 5/30
604/68

(Continued)

FOREIGN PATENT DOCUMENTS

WO WO-2016102407 A1 6/2016

OTHER PUBLICATIONS

International Search Report (in English and German) and Written Opinion of the ISA (in German) issued in PCT/IB2018/058813, mailed Feb. 27, 2019; ISA/EP.

(Continued)

*Primary Examiner* — Emily L Schmidt
*Assistant Examiner* — Antarius S Daniel
(74) *Attorney, Agent, or Firm* — Harness, Dickey & Pierce, P.L.C.

(57) ABSTRACT

A method and a device for needleless injection of liquid into a substrate, in particular of a liquid pharmaceutical or cosmetic preparation into a biological tissue, which makes it possible in a particularly advantageous manner to reliably inject a particularly fine liquid jet into the substrate without a significant increase in the static pressure in the liquid during the injection process. According to the invention, this is achieved by first accelerating the liquid received in a liquid container together with the latter to an initial velocity before the movement of the liquid container is stopped again, while simultaneously ejecting the liquid from the liquid container through an outlet nozzle under at least partial retention of its movement. Preferably, the ejected liquid jet is set in rotation about its jet axis before it impinges on the substrate, so that the jet receives a helical movement and thus practically drills into the substrate without splashing away laterally.

18 Claims, 10 Drawing Sheets

Figure 2B:
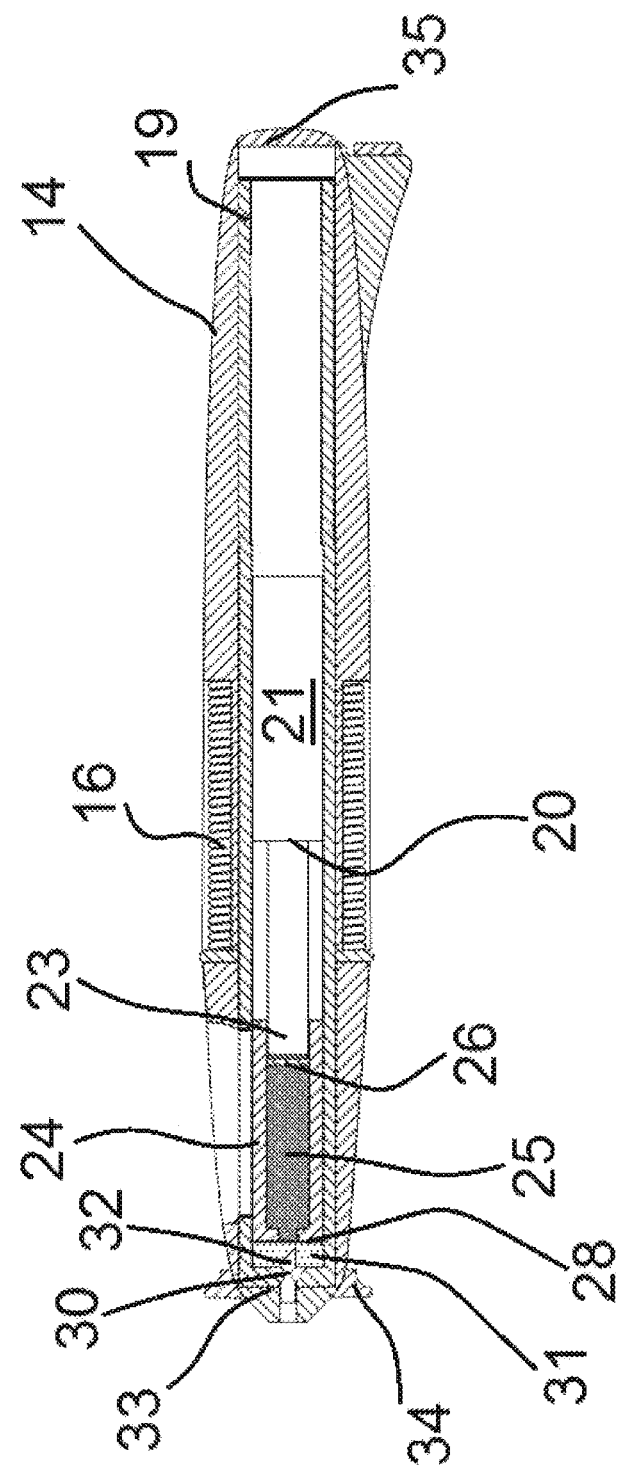

(52) U.S. Cl.
CPC .............. *A61M 2005/31588* (2013.01); *A61M 2205/8206* (2013.01); *A61M 2205/8287* (2013.01); *A61M 2250/00* (2013.01)

(58) Field of Classification Search
CPC ........ A61M 2005/31588; A61M 5/178; A61M 5/20; A61M 5/2459; A61M 5/2466; A61M 5/285; A61M 5/286; A61M 5/288; A61M 2005/2462; A61M 2005/247; A61M 2005/2474; A61M 2005/287; A61M 11/00; A61M 11/007; A61M 11/008
See application file for complete search history.

(56) References Cited

U.S. PATENT DOCUMENTS

| | | | | |
|---|---|---|---|---|
| 5,569,190 | A * | 10/1996 | D'Antonio | A61D 7/00 604/71 |
| 6,132,395 | A * | 10/2000 | Landau | A61M 5/30 604/249 |
| 6,224,567 | B1 * | 5/2001 | Roser | A61M 5/30 604/218 |
| 2002/0143323 | A1 | 10/2002 | Johnston et al. | |
| 2006/0149193 | A1 | 7/2006 | Hall | |
| 2010/0016827 | A1 * | 1/2010 | Hunter | A61M 5/30 604/67 |
| 2016/0250423 | A1 * | 9/2016 | Casale | A61M 5/30 128/200.23 |
| 2017/0312435 | A1 | 11/2017 | Stefansen et al. | |
| 2018/0099140 | A1 * | 4/2018 | Tavger | A61M 35/003 |
| 2020/0122173 | A1 * | 4/2020 | Adam | A61M 5/2466 |

OTHER PUBLICATIONS

U.S. Appl. No. 16/762,186, filed May 7, 2020, Fritz Schmitt.
U.S. Appl. No. 16/762,189, filed May 7, 2020, Fritz Schmitt.

* cited by examiner

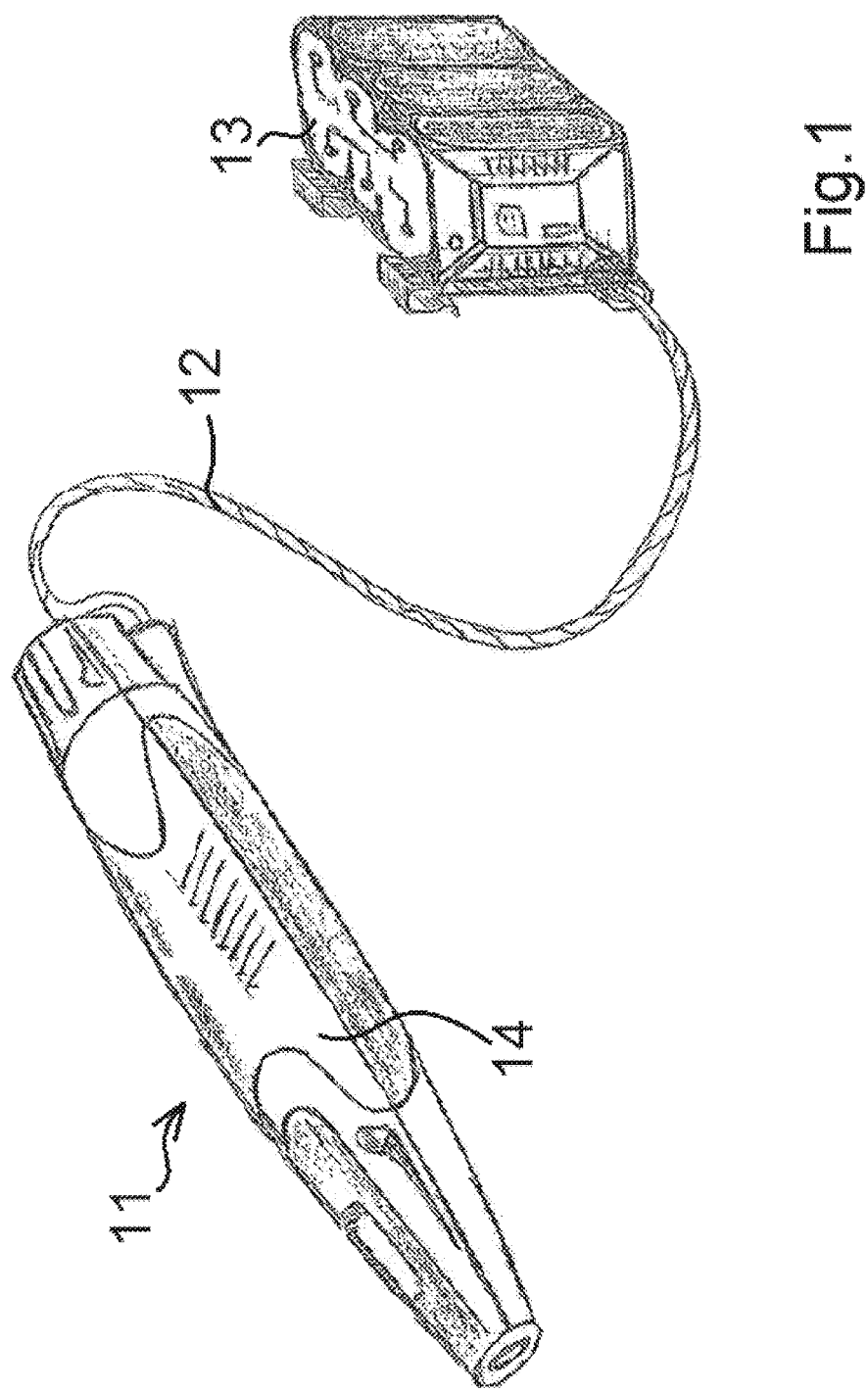

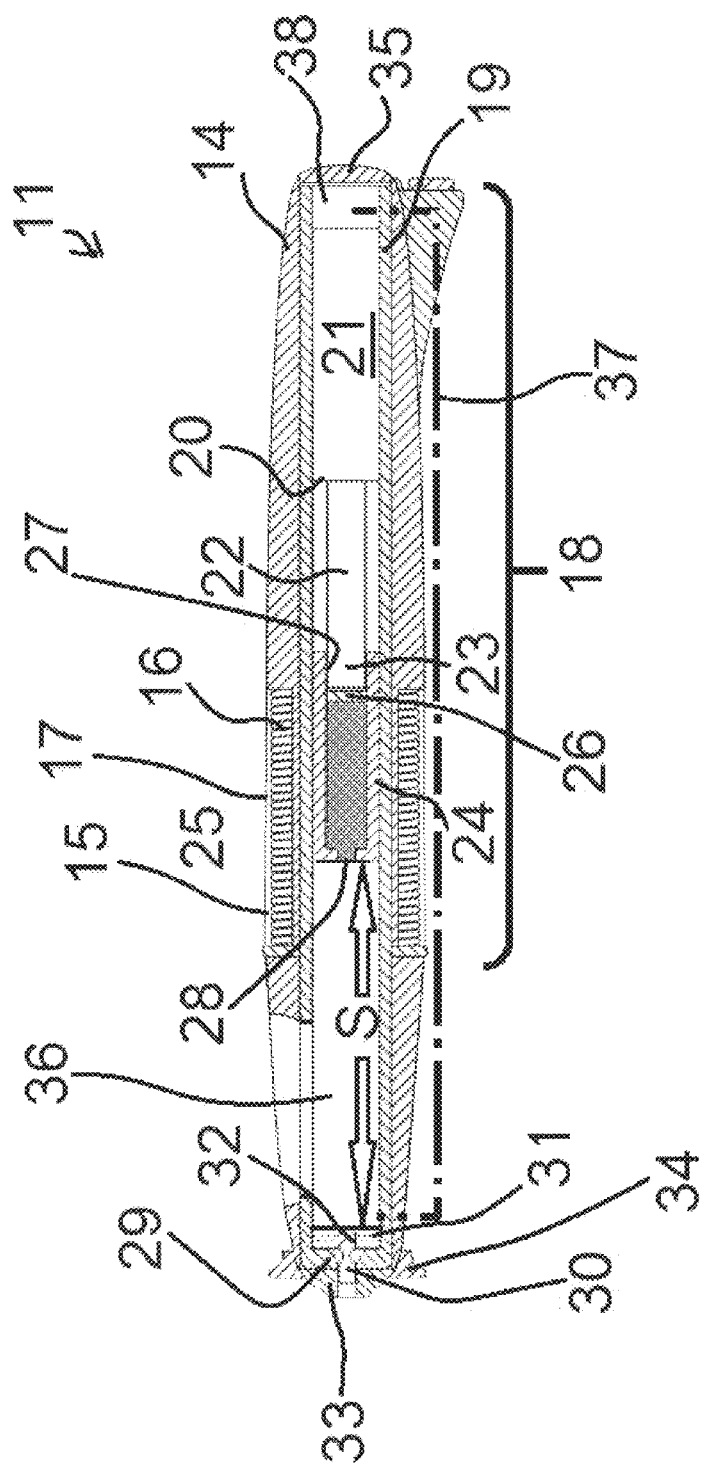

METHOD AND DEVICE FOR THE NEEDLE-FREE INJECTING OF FLUID INTO A SUBSTRATE

CROSS-REFERENCE TO RELATED APPLICATIONS

This application is a 371 U.S. National Phase of International Application No. PCT/IB2018/058813, filed on Nov. 9, 2018, which claims the benefit of German Patent Application No. 10 2017 126 493.0, filed on Nov. 10, 2017. The entire disclosures of the above applications are incorporated herein by reference.

BACKGROUND

This section provides background information related to the present disclosure which is not necessarily prior art.

TECHNICAL FIELD

The invention relates to a method for needleless injection of liquid into a substrate, in particular a liquid, pharmaceutical or cosmetic product into a biological tissue, in which the liquid is ejected from a liquid container through an outlet nozzle and exits this outlet nozzle at a high ejection velocity as a liquid jet which enters the substrate. The invention further relates to an injection device for needleless injection of liquid into a substrate, in particular of a liquid, pharmaceutical or cosmetic product into a biological tissue, comprising a housing for accommodating a liquid container containing the liquid and ejector device for ejecting the liquid from the liquid container though an outlet nozzle. To inject a liquid into a substrate, for example a liquid pharmaceutical or cosmetic product into or under the skin of a human or other living being, the liquid is usually injected through an injection needle into the substrate, i.e. the human or animal tissue. For this, the injection needle must first penetrate into the substrate. As a result of the incision made by a cutting edge at the needle tip, injuries occur which, although they usually heal quickly in living tissue, regularly result in scar formation. Furthermore, injections with injection needles always carry the risk of infection.

DISCUSSION

There have therefore been various experiments in the past with hypodermic jet injection devices for needleless injection to bring a small amount of liquid, such as a vaccine or other drug, an anesthetic or the like, directly through the skin surface into the tissue while forgoing the use of an injection needle that can penetrate into the substrate. Basically, the idea behind these efforts was to penetrate the patient's skin solely by the pressure of the liquid and to bring the injection medium to a desired depth. However, most of the devices developed for this purpose were not able to fulfil the expectations placed on them at all, or at least not satisfactorily.

The injection devices proposed in the past for needleless injection of liquids such as drugs have an energy storage such as a spring mechanism, a pressure reservoir and/or a detonator which, when triggered, causes a pressure increase in a liquid supply contained in the device in order to eject liquid from the supply through an outlet nozzle. The nozzle cross-section is as small as possible and the pressure acting on the liquid supply is as high as possible in order to produce a liquid jet with a small cross-section and high jet velocity.

Due to the very sudden, large static pressure increase that occurs when the energy storage in the liquid supply is triggered, an undesirable change and/or damage to the liquid can easily occur, e.g. due to the fact that the sudden, large pressure increase in the liquid causes molecules of pharmaceutical active ingredients contained in the liquid to break up, thereby changing their effectiveness or losing it completely, without this being detectable when injecting through the skin of a patient. It is then unclear whether and to what extent an active substance previously present in the liquid container in a known quantity can actually achieve its intended effect after being injected into the tissue.

From US 2002/0143323 A1 an endoscopic device for gastrointestinal epithelial removal is known, in which a probe is supplied with a liquid. The liquid is supplied to the probe from a supply container which can be acted on by a pressurized gas from a gas bottle. US 2006/0149193 A1 discloses a device with a probe and a liquid applicator, which has a liquid outlet for needleless injection of a liquid into a biological tissue and a liquid conduit leading to the liquid outlet. An associated liquid delivery device has a drive device and is connectable to a pressure storage pressure container as energy storage. The liquid delivery device includes an expansion chamber which has a movable wall surface which encloses the liquid to be injected and which can be acted upon by a pressurized liquid.

Furthermore, devices are known which are used for needleless injection of a liquid under the mucosa. For example, US 2009/0157114 A1 discloses an endoscope with a probe for needleless injection under the mucosa. For this purpose, the probe emits a jet of a sodium chloride solution, which penetrates the tissue due to its small cross-section and concurrently high velocity. A pump unit or, optionally, a force-enhancing lever is provided to convey the sodium chloride solution and generate the respective pressure.

SUMMARY

This section provides a general summary of the disclosure, and is not a comprehensive disclosure of its full scope or all of its features.

The aspect of the invention is therefore to provide a method and a device of the aforementioned type with which the liquid is treated as gently as possible during the injection process.

This aspect is achieved with the method according to the invention by accelerating the liquid container together with the liquid contained therein to an initial velocity before the liquid is ejected from the liquid container through the outlet nozzle. In an advantageous embodiment, the movement of the liquid container after acceleration to the initial velocity is then stopped while at least a partial quantity of the liquid contained therein continues to be moved and is ejected through the outlet nozzle. At the beginning of its ejection from the liquid container, the liquid or its partial quantity is already moving at an ejection velocity, i.e. it already has a kinetic pressure component by which the (static) pressure increase that can occur in the entire system during injection is reduced. The amount of static pressure increase in the liquid depends essentially only on the shape and the degree of cross-sectional constriction which the ejected liquid passes through on its way out of the liquid container through the outlet nozzle, i.e. on the flow resistance which the outlet nozzle exerts against the liquid ejected through it. In an advantageous embodiment of the invention, before and/or while passing through the outlet nozzle, the liquid jet can be set in rotation about its jet axis at least on its outer circumference, whereby a widening, i.e. an increase in cross-section, of the liquid jet on its way from the injection device to the substrate surface and the mushrooming repeatedly observed with the known devices when impinging on the substrate is very reliably avoided. It is assumed that centripetal forces acting as a result of the rotation hold the liquid particles (molecules) together, not only on the path of the liquid jet from the outlet nozzle to the substrate surface, but also when penetrating the substrate. In fact it seems that, at least if the outlet nozzle is suitably designed, the rotation of the jet after its exit from the outlet nozzle even leads to a reduction of the cross-section and thus to an increase in the velocity of the liquid jet, so that the liquid jet can impinge on the substrate even at a higher velocity than it has when exiting an outlet nozzle. Experiments have shown that the liquid jet reliably penetrates biological tissue such as the skin of a human or animal when injecting, even if the outlet nozzle of the device according to the invention is positioned at a distance from the tissue surface, i.e. the liquid jet has to bridge the distance between the nozzle and the tissue surface as a "free jet", without an increase in the distance having a negative effect on the injection quality. The rotation, which is imposed on the jet before it impinges on the substrate, is superimposed on the translatory movement of the liquid in its jet direction to form a helical movement, with which, according to the observations made, the jet practically "drills" or "screws" itself into the substrate with very low resistance at the surface of the substrate, forming an inlet channel corresponding to the jet cross-section, wherein in fact practically none of the liquid impinging on the substrate is lost, i.e. does not penetrate into the substrate.

The injection device of the aforementioned type according to the invention, by means of which the above-mentioned method according to the invention can be carried out, is characterized by an acceleration device for accelerating the liquid container with the liquid contained therein to an initial velocity inside the housing and a deceleration device for stopping the movement of the liquid container. By means of the acceleration device, the liquid container including the liquid contained therein can first be accelerated to the initial velocity before the deceleration device decelerates the movement of the liquid container again, for example by a stop acting between the housing and the liquid container, while however the movement of the liquid contained in the container is at least partially maintained, so that the liquid thus leaves the liquid container and exits through the outlet nozzle. The stop, which is part of or substantially forms the deceleration device, may be provided with a stop damper, for example an elastomeric buffer element. In this way, the deceleration of the liquid container is not abrupt, but according to the damping capacity of the stop damper, thus reliably preventing damage to the container, which may be made of a fragile material such as glass.

In an advantageous embodiment of the invention, it is provided that the liquid container has a cylinder space containing the liquid, into which the pressure piece can be inserted. The liquid container can thus be designed in the manner of a cylindrical ampoule (carpule), as is used for cylindrical ampoule syringes, for example in dentistry. The liquid container can have a container outlet adapted to an inlet cross-section of the outlet nozzle. It is possible in a particularly advantageous manner for the liquid container to be closed on its outlet side with a pierceable plug which can be pierced by a hollow needle, which is preferably provided on the inlet side of the outlet nozzle, in order to open the liquid container, at a point in time after the liquid container together with the liquid contained therein has been accelerated to the initial velocity, i.e. in particular when the movement of the liquid container is stopped again. The opening of the cylindrical ampoule (liquid container) which then takes place when the hollow needle pierces the piercing plug allows the liquid to be moved further out of the liquid container through the hollow needle (flow through) and to be ejected through the outlet nozzle connected to the outlet side of the hollow needle. It is also possible for the hollow needle to be formed in one piece with the outlet nozzle or to form the outlet nozzle itself.

The container outlet may have an acceleration zone which preferably converges from the cross-section of the cylinder space towards the inlet cross-section of the outlet nozzle, thus further accelerating the liquid as it exits the liquid container. When the outlet nozzle is arranged or arrangeable in a particularly advantageous manner integrally or replaceably on the liquid container, it follows the movement and deceleration of the container during the injection process.

The ejector device may have an electromagnetically, chemically and/or gas operated drive, also a drive with a preloaded compression spring is usable for the invention. An electromagnetic drive has proved to be particularly suitable for this purpose, with which it is possible to accelerate the liquid container together with the liquid contained therein to a very high speed within a very short time and thus over a very short distance, before the liquid container is then decelerated again by the deceleration device, while the co-accelerated liquid (or at least a partial quantity of the liquid) leaves the container then open at its outlet without any significant (static) increase in pressure, simply by continuing its movement. By means of an electromagnetic drive, it is also advantageously possible not only to move the liquid container translationally in the axial direction, but also to set it in rotation and thus to cause the liquid jet to leave the outlet nozzle with the rotation around its jet axis described above.

Preferably, the liquid container is replaceably accommodatable in the housing.

For when the liquid supply is contained in a liquid container, for example in the form of a cylindrical ampoule (carpule), which is replaceably accommodated in the housing, not only different liquids can be injected with one and the same device with the least possible effort, for example liquid pharmaceutical products of different types, as may be required for a series of vaccinations, by simply subsequently inserting containers with different liquids into the device. The arrangement also has the advantage that the device can be cleaned and/or sterilized particularly easily and thoroughly without the liquid container accommodated in it, which is particularly important for its use in pharmaceutical areas, but also in the (commercial) cosmetic sector.

As mentioned above, it has proven to be very advantageous when the outlet nozzle is arranged on the liquid container. This arrangement allows the type and shape of the nozzle, in particular the passage for the liquid provided therein, to be adapted in the best way possible to the specific liquid contained in the liquid container and to be injected. For example, when processing liquids of comparatively high viscosity, such as hyaluronic acid products used in cosmetic applications, e.g. for wrinkle injection or lip modelling, and in medicine for injection into joints damaged by arthrosis, it may be necessary to provide a nozzle with a larger passage cross-section than for injecting simple physiological saline solution. The arrangement of the outlet nozzle directly on the liquid container then ensures that the appropriate outlet nozzle for the respective liquid absorbed in the container is used in any case. For reasons of hygiene in particular, it is preferred that the liquid containers used in the injection device according to the invention, especially those with outlet nozzles arranged thereon, are disposable containers which are disposed of after a single use, i.e. are not refilled.

The outlet nozzle can have a nozzle outlet running essentially coaxial to the housing axis of the housing. The liquid then exits in a direction coaxial with the housing axis of the housing and thus generally perpendicular to the surface of the substrate, because the housing is generally oriented perpendicular to the substrate surface, for example a skin surface, when the device is handled. However, it is also possible, in a particularly advantageous manner, for the outlet nozzle to have a nozzle outlet which runs at an angle to the housing axis, the angle preferably being greater than 45°. It is particularly advantageous if the nozzle outlet runs in a direction which is in the range of more than 75° up to a right angle (or even beyond), i.e. the outlet direction runs essentially in a plane normal to the housing axis of the housing. When the orientation of the housing is substantially constant, i.e. approximately perpendicular to the substrate surface, this embodiment of the invention allows the liquid to be injected into the substrate substantially parallel to the substrate surface and closely below it, which is particularly easy to achieve, when the substrate, such as the skin of a human being, is pliable in its upper layer and can be depressed a certain distance in a trough-like manner by means of the device so that the nozzle outlet is then located in this trough-like forming depression below the level of the adjacent substrate and then the liquid can be injected substantially parallel to the substrate surface below this substrate surface. In particular for such an outlet nozzle, it or the front end of the housing may be provided with a depth indicator or a depth stop so that the liquid can be injected to the exact depth required below the substrate surface.

According to the invention it is provided in a particularly advantageous way that the liquid container with the liquid contained therein together with an ejector plunger of the ejector device is movably accommodated in the housing or an acceleration path provided in the housing, respectively, and that a stop acting between the housing and the liquid container is provided, e.g. at its front outlet end. This embodiment according to the invention has the advantage that the liquid container together with the liquid contained therein is first accelerated together with the ejector device in the housing before the liquid is ejected from its container through the outlet nozzle. This limits the pressure increase in the liquid when actuating the ejector device to eject the liquid by first imposing a dynamic pressure component on the liquid. Especially in the case of pressure-sensitive liquids, this can reduce or completely avoid the risk of damage. In order to slow down the (static) pressure increase in the liquid when the liquid container hits the stop, it is advantageous when a stop damper, for example an elastomeric buffer element, acting between the stop and the liquid container is provided.

The ejector device with electromagnetic drive, which has its independent inventive merit, is also ideally suited for placing a series of injections in a short time sequence at different, preferably immediately adjacent points in the substrate. For this purpose, the ejector plunger is moved back into its initial position immediately after ejecting a partial quantity of liquid from the liquid supply, preferably by briefly reversing the direction of the current in the coil, and is thus ready for a further injection within a very short time, for which it is accelerated again in the injection direction by means of the electromagnetic coil and again for ejecting a partial quantity of liquid from the liquid supply. A liquid container formed in the manner of a cylindrical ampoule (carpule), forming a cylinder space with a liquid outlet provided on a side and a piston actuatable by the ejector plunger, which piston is insertable into the cylinder space in steps effected by the plunger hitting it, in order to always eject a partial quantity of liquid from the liquid outlet, which liquid then exits the device through the outlet nozzle, is particularly suitable for carrying out such series injections. As the piston is pushed increasingly deeply into the cylinder space of the liquid container by the ejector plunger with each injection step, the acceleration section available to the ejector plunger between a rear, constant stop in the housing and its stop at the front, defined by the piston, is step-wise increased. Since the increase of the acceleration section with otherwise unchanged general conditions, in particular constant electric current applied to the electromagnetic drive, would result in an increasingly greater velocity of the plunger and the liquid moved together with it when hitting the stop, the jet velocity imposed in the liquid and thereby its penetration depth into the tissue would then also increase, means are preferably provided for adapting the initial velocity of the liquid container, which means make it possible, irrespective of the position of the piston in the liquid container, to repeatedly accelerate the latter together with the liquid (yet) contained therein at least approximately to an equally large initial velocity, so that the injections generated in series each penetrate the substrate to the same depth. The device according to the invention is thus advantageously suited for injecting under wrinkles in the skin of a patient or for producing tattoos which can be produced needle-free with the invention.

It is also possible that the electromagnet and/or the energy storage (battery/accumulator) intended for its operation are located on the moving part of the ejector device, i.e. in particular the ejector plunger, and can be removed from the housing together with it, e.g. in order to clean and/or sterilize the housing before using the device again.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 2C:
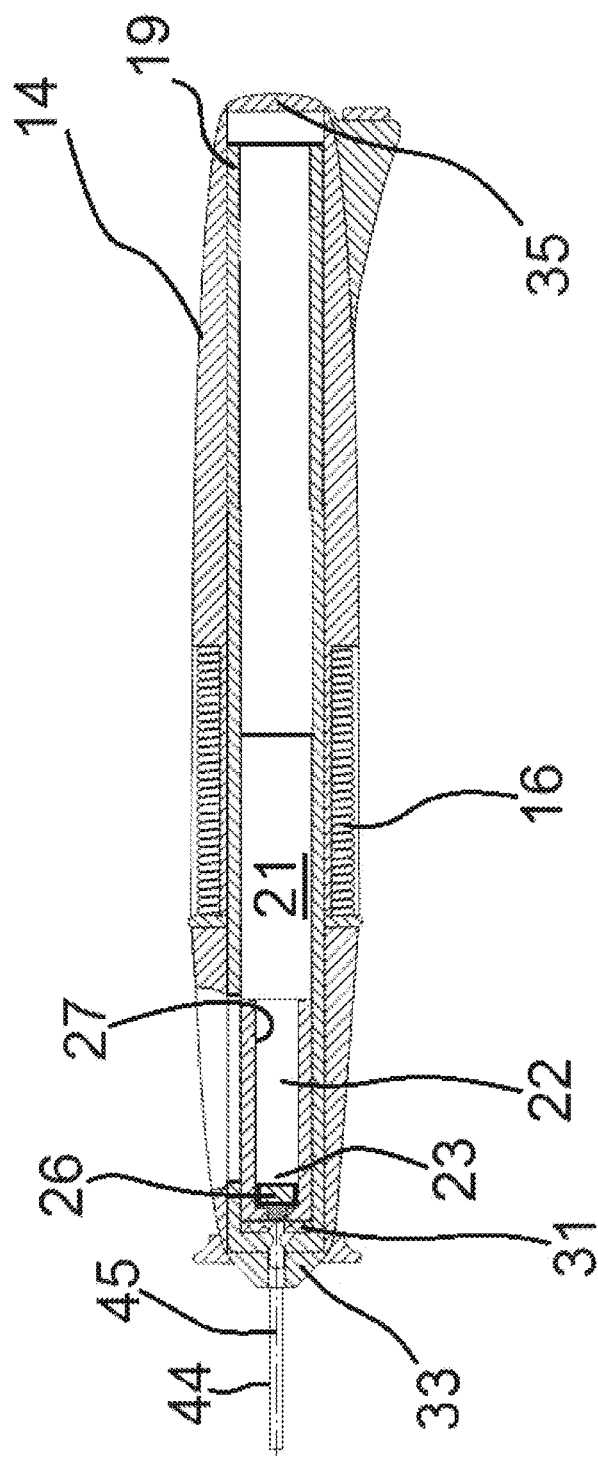
Figure 3:
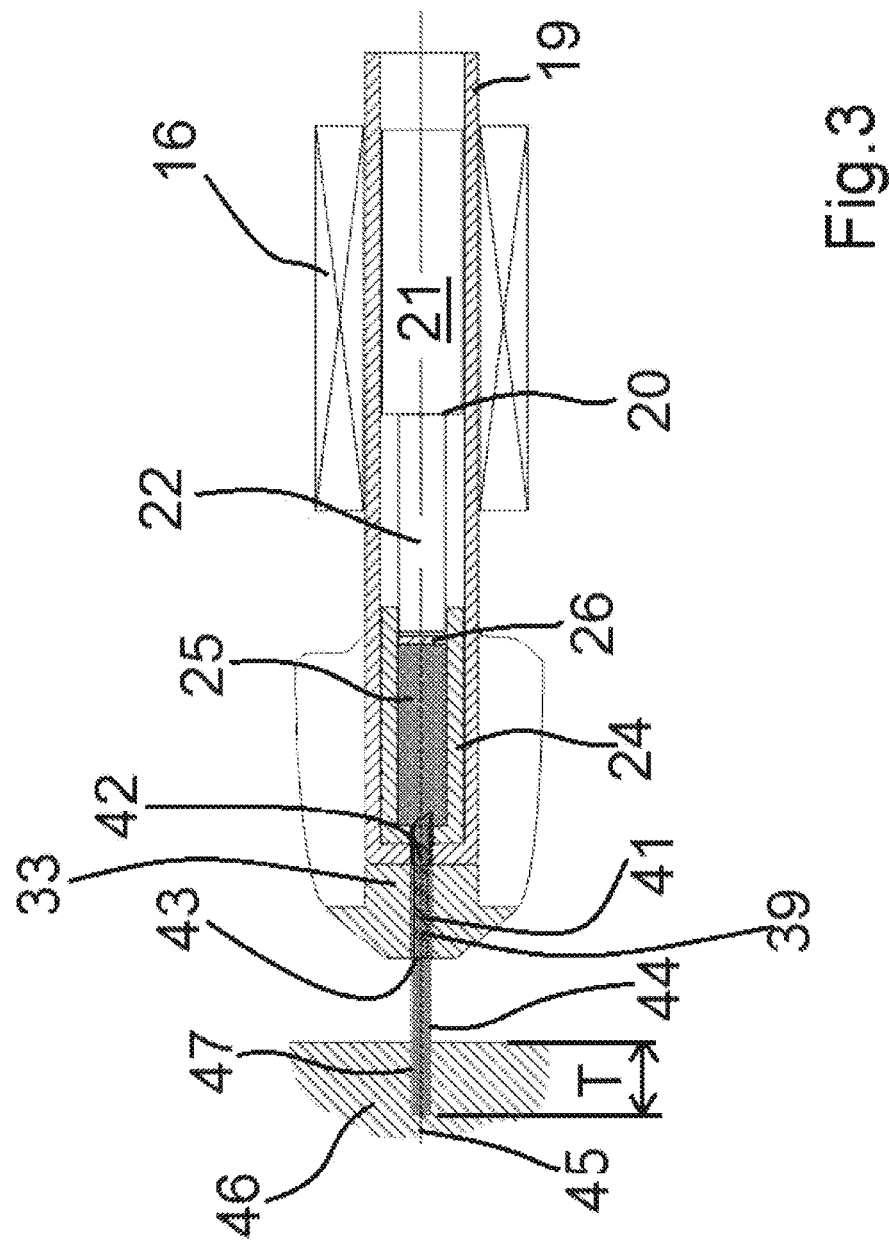
Figure 4:
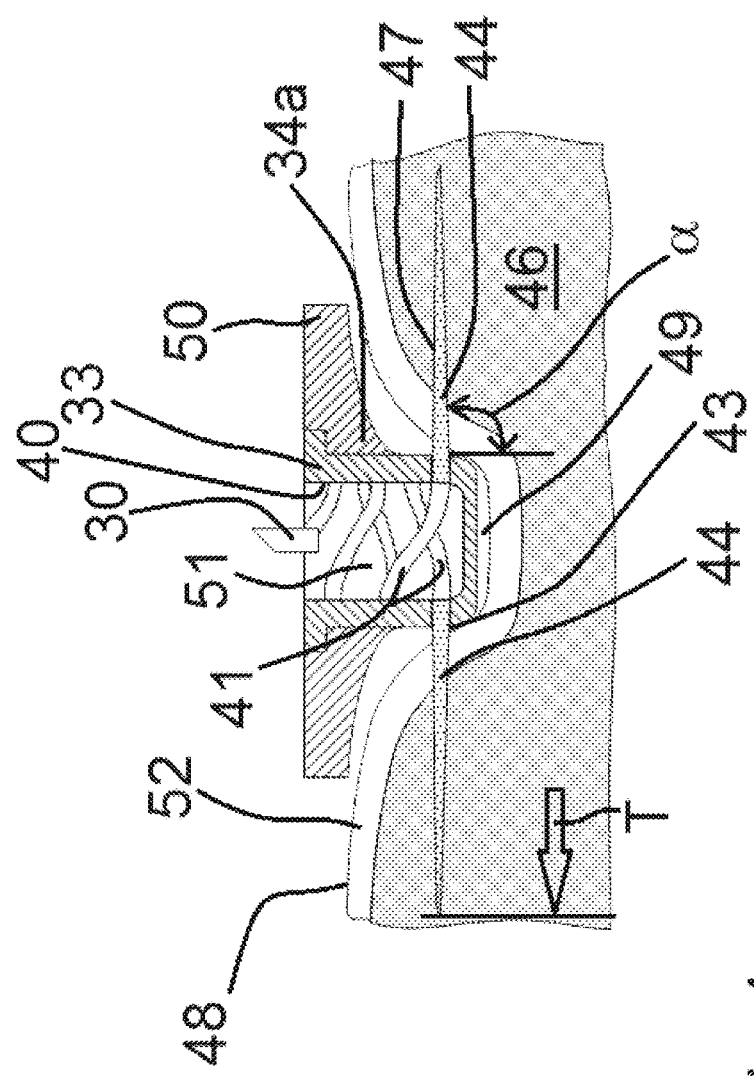
Figure 5:
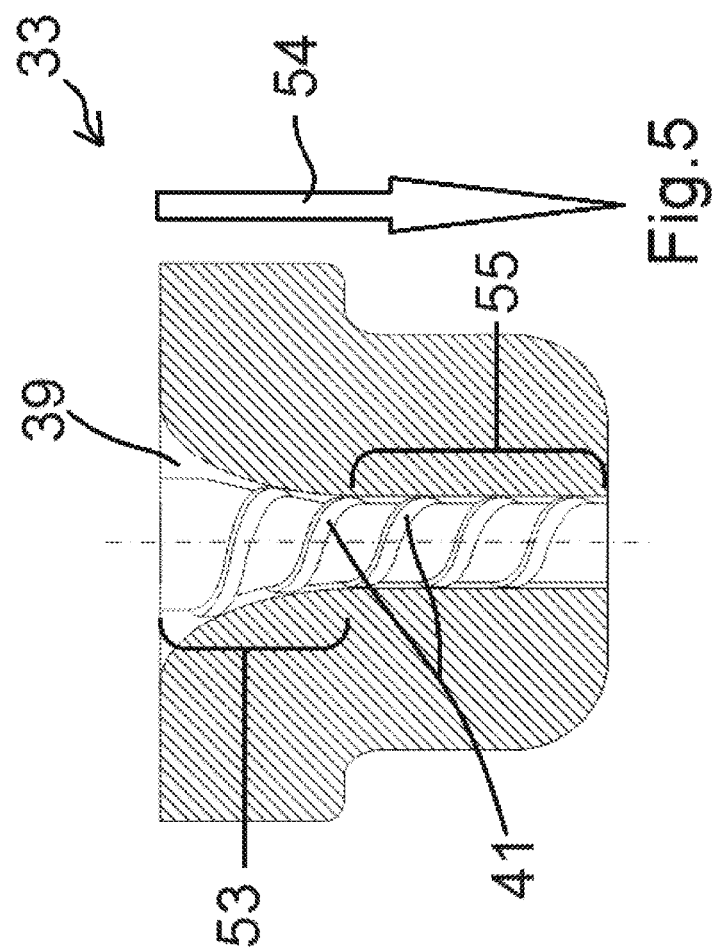
Figure 6:
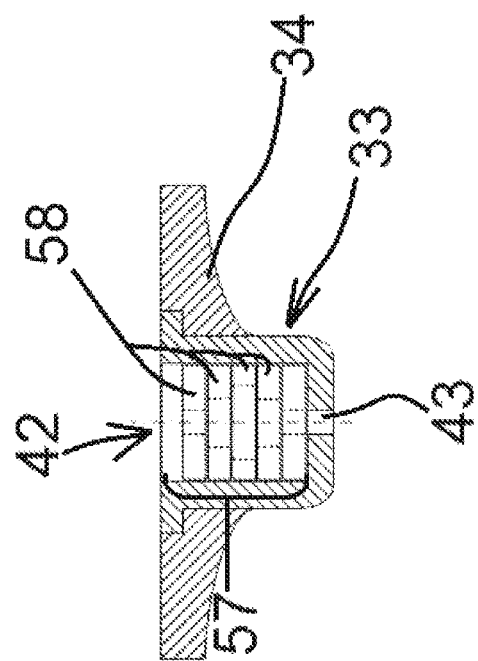
Figure 7:
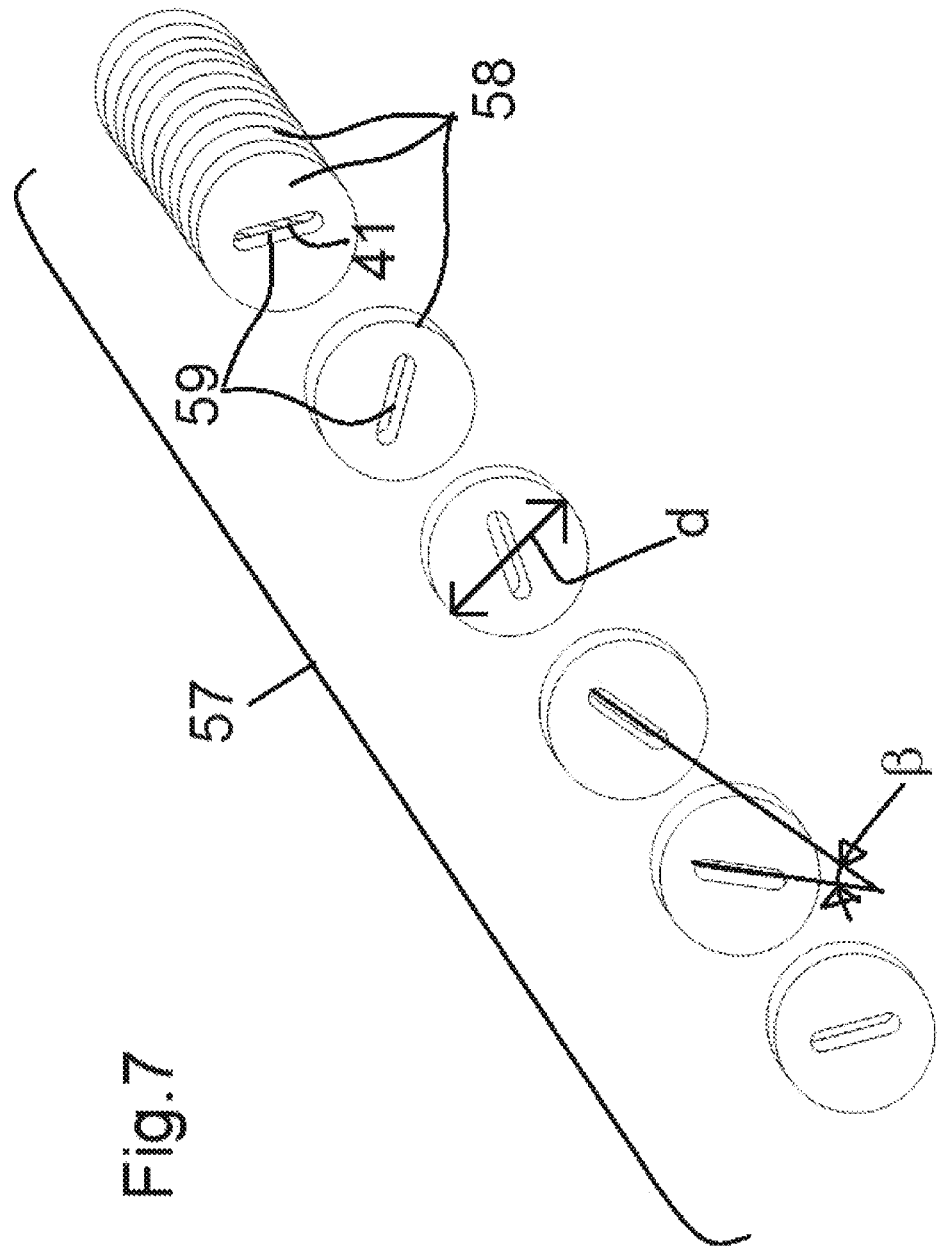
Figure 8:
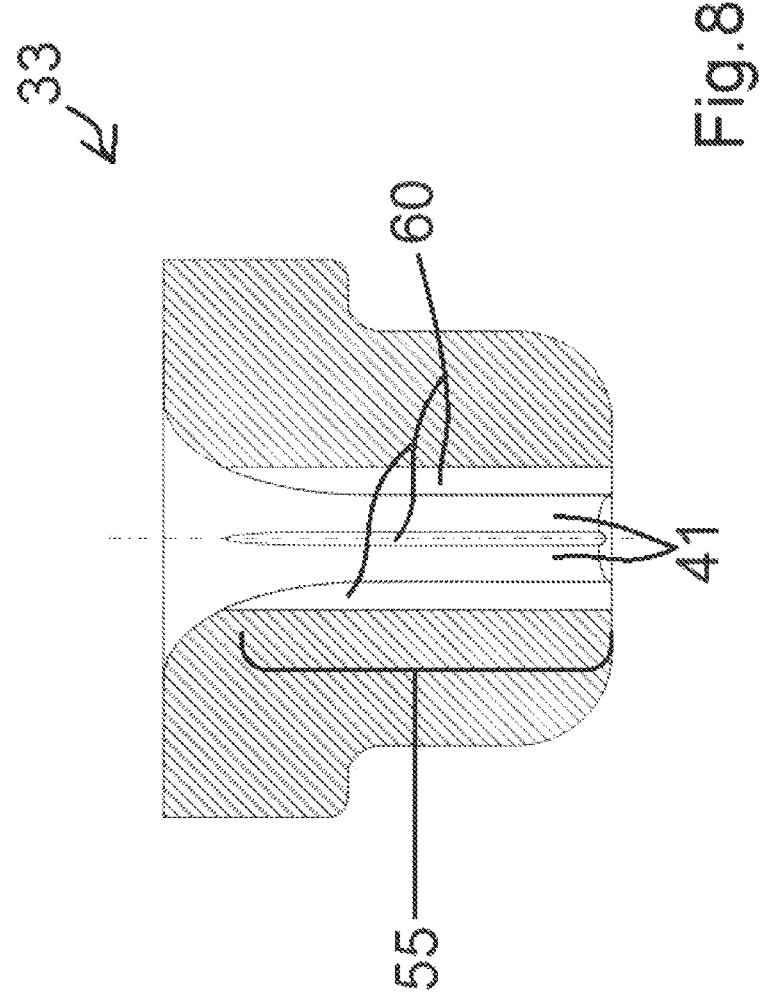

Further features and advantages of the invention result from the following description and figure, in which preferred embodiments of the invention are presented and explained in more detail by means of examples. These show:

FIG. 1 a general representation of an injection device according to the invention in perspective view;

FIG. 2a-c the handling part of the injection device according to FIG. 1 in longitudinal section in different operating positions of the ejector device;

FIG. 3 the ejector device with a first version of an outlet nozzle used in the invention, in longitudinal section;

FIG. 4 a second embodiment of an outlet nozzle for use with the device according to the invention in section;

FIG. 5 a third embodiment of an outlet nozzle for use with the device according to the invention in section;

FIG. 6 a fourth embodiment of an outlet nozzle for use with the device according to the invention in section;

FIG. 7 the orifice plates of the orifice plate stack used in the embodiment according to FIG. 6 in a perspective, expanded representation (exploded view); and FIG. 8 a fifth embodiment of an outlet nozzle for use with the device according to the invention in section.

DETAILED DESCRIPTION

Example embodiments will now be described more fully with reference to the accompanying drawings.

In FIG. 1, 10 refers to an injection device as a whole according to the invention, which has a handling part 11, which is connected via a cable connection 12 to an external power supply 13, a battery pack in the embodiment shown.

The handling part 11 of the injection device 10 can be conveniently handled by its user with a single hand. The more detailed structure of the handling part 11 is clearly visible in the sectional view according to FIG. 2a to c. Accordingly, it has a housing 14 which is provided with a recess 15 on its outer circumference in which a magnetic coil 16 is accommodated. The magnetic coil 16 is protected by a circumferential cover 17.

The magnetic coil 16 is part of an ejector device referred to as 18 in its entirety, which further comprises an ejector tube 19 made of plastic material inserted into the housing and passing through it essentially from its rear end (right in the figure) to the front (left) outlet end, and an ejector plunger 20 guided therein in a longitudinally displaceable manner, which in the embodiment shown has a rear section 21 and a front section 22. While the rear section with a larger diameter is adapted to the internal cross-section of the ejector tube 19 and can slide in it with as little play and friction as possible, the front section 22 has a smaller diameter. It forms a pressure piece 23 which can be inserted or is insertable from behind into a cylindrical liquid container 24 in the form of a liquid round or cartridge (carpule) containing a liquid 25 to be injected into a substrate, for example into or under the skin of a human or animal. This liquid container 24, similar to the rear section 21 of the ejector plunger 20, is accommodated in the ejector tube 19 substantially without play, so that it can also slide easily in the latter. At the rear (i.e. on the right in the figure), the liquid container 24 is closed by a slidable piston 26, which holds the liquid 25 in the container 24 and is pushed into the cylinder space 27 defined by the container 24 to such an extent that the pressure piece 23 also fits a little into this cylinder space at its rear. On its left outlet side, as shown in the figure, the liquid container 24 is closed with a membrane 28 or an elastic rubber plug.

The ejector tube 19 is fitted with a cap 29 at its front end, left-hand side in FIG. 2, which has a central opening in which a piercing cannula 30 projecting inwards towards the liquid container 24 is accommodated. An elastic buffer element 31 surrounding the piercing cannula 30 is arranged inside the cap.

The piercing cannula 30 protrudes with its outlet side end opposite its piercing tip 32 somewhat beyond the cap 30 and thus forms a centering for an outlet nozzle 33, which is fitted onto this outlet side end of the cannula 31 and fixed to the housing 14 by means of a union nut 34.

In order to prepare the device for use, the ejector plunger 20 with its front section 22, which forms the pressure piece 23, is first inserted from behind into the cartridge-like liquid container 24, wherein the front side of the pressure piece 23 contacts the piston 26 in the cylindrical opening of the liquid container. This assembly of liquid cartridge 24 and ejector plunger 20 can then be inserted with the membrane 28 in front, which closes the liquid cartridge at the front, from behind into the ejector tube 19 in the housing 16, for which purpose a cover cap 35 arranged at the rear of the housing can be opened. After closing the cover cap the device is ready for operation. This operating state is shown in FIG. 2a.

Based on the FIGS. 2a to 2c, the operation of the device according to the invention can be easily understood during injection. Although it happens very quickly, the injection process actually takes four different phases. The first phase is the set-up phase shown in FIG. 2a. The second phase is the initial acceleration of the cartridge 24 as shown in FIG. 2b. The third phase is to eject a first partial quantity of the liquid 25 from cartridge 24 due to the momentum of the accelerated liquid at high velocity, The fourth phase is to eject a second partial quantity of the liquid 25 remaining in cartridge 24 at a lower velocity as shown in FIG. 2c by the front plunger section 22. FIG. 2a shows the initial position of the ejector device, in which the rear section 21 of the ejector plunger 20 is in the rearmost position (in the figure on the right) (rear end position). The free space in the ejector tube 19 which extends in this position of the ejector plunger and the liquid container placed on the front of the ejector plunger up to the end cap 29 forms an acceleration section S, over the length of which the assembly consisting of plunger and liquid container 24 can be accelerated. In order to trigger an injection from the position shown in FIG. 2a, the magnetic coil 16 is supplied with electric energy from the battery pack 13 and thereby accelerates the ejector plunger 20 with the liquid cartridge 24 attached to the front of it over the acceleration section S in a direction of movement towards the outlet nozzle (to the left in the figure as shown in FIG. 2b). The accelerated assembly reaches a very high velocity in a very short time, which in practice can be over 500 m/s, and even over 800 m/s with a suitably longer acceleration section. The liquid container 24 with the liquid 25 contained in it first follows this movement until it is decelerated by the buffer element 31, which is compressed between the front cap 29 of the ejector tube 19 and the assembly of ejector plunger 20 and liquid container 24 moved at high velocity by the magnetic coil 16 towards the outlet nozzle 33. The main purpose of the buffer element 31 is to prevent the liquid container striking against the front cap 29 from jumping back from it. The position of the ejector device in this operating state is shown in FIG. 2b.

As is only schematically indicated by dotted lines in the illustrations according to FIG. 2a, the free space 36, which is present inside the ejector tube 19 between its front cap 29 and the front end of the liquid container 24 closed by the membrane, is connected to the space 38 behind the rear plunger end 21 by means of an overflow line 37. Through the overflow line, air can be displaced from the front free space 36 or actually actively sucked out by the negative pressure in space 38 which forms behind the plunger during its forward movement, thus ensuring that the ejector plunger 20 with the liquid container 24 is not slowed down due to increased air resistance. In the practical implementation of this feature, the overflow line can be integrated into the wall of the housing so that it is actually not noticeable from the outside.

As soon as the piercing tip 32 of the piercing cannula 30 pierces the membrane 28 provided at the front end of the liquid container 24, an initial first quantity of the liquid 25 contained in the container can emerge from the front end of the container and pass through the cannula 31 into the outlet nozzle 33. Since the membrane 28 of the liquid container 24 is pierced at a point in time at which the liquid 25 contained in the container is yet moving at a high velocity, the movement of the liquid container 24 stops very abruptly when hitting the buffer element 31, when the buffer element 31 is compressed as much as possible. However, the static pressure increase in the liquid volume contained in container 24 remains small, because the kinetic energy imposed on the liquid during acceleration is only partially converted into static energy (pressure increase). Rather, at least a first partial quantity of the liquid contained in the container enters with the initial velocity, to which it (together with the liquid container) has been accelerated, first the cannula and from there the outlet nozzle, which it then exits again at the outlet side of the outlet nozzle a high orifice velocity corresponding to the high total pressure (=sum of kinetic and static energy) when opening the liquid container at the outlet side of the outlet nozzle, ambient pressure being imposed on the liquid at the outlet side of the outlet nozzle and the inherent (total) pressure energy being converted into kinetic energy (velocity). In practice, the outlet nozzle used, which is preferably designed as described below, can have a passage 36 for liquid 25 with a diameter of 80 to 300 μm, so that the ejected liquid impinges as a very fine liquid jet with a correspondingly small cross-section on the substrate at a very high velocity. The exit velocity of the liquid can easily reach 1000 m/s. With this extremely fast and thin liquid jet, an injection channel is created (shot) in the substrate to a depth that depends on the jet velocity and its diameter and thus ultimately on the velocity to which the ejector plunger has accelerated the liquid supply.

In the fourth phase of the injection process when the entire quantity of liquid is to be injected into the substrate at an injection point, the magnetic coil 16 can continue to be powered after reaching the front end position of the liquid container 24 (FIG. 2c). This causes the ejector plunger 20 with its front section 22 (pressure piece 23) to be pressed further from behind against the piston 26 in the liquid container so that the liquid (second partial quantity) still remaining in the container after the pressure has decayed by ejecting a first quantity is pressed through the cannula 30 as with a conventional syringe and then ejected through the outlet nozzle 33. Surprisingly, it has been found that despite the significantly lower pressure or the lower velocity, respectively, with which the second partial quantity is then ejected, the second partial quantity reliably and completely penetrates into the injection channel created in the substrate previously by means of the first partial quantity and thus reaches into the substrate, i.e. in the embodiment into or under the skin. This generally leads to a depot formation at the end of the injection channel, i.e. the second partial quantity of liquid is distributed substantially evenly in the tissue in a spherical shape around the end of the injection channel. The injection can be continued until plunger 26 is fully inserted from pressure piece 23 to the front end of the liquid container (FIG. 2c).

If desired, a sequence of more or less closely positioned injections of comparatively small amounts of liquid can be made at short intervals with the device. For this purpose, the ejector plunger 20 is pulled back into its initial position (i.e. to the right in the figure) by suitable control (changing the direction of electrical current) of the magnetic coil 16 directly after generating a pulse shock in the liquid contained in the container. Since the liquid container 24 is already open from the piercing tip 32 of the cannula 30 at the membrane after the very first injection carried out as described above, in this mode of operation it can remain in its left-hand end position as shown in the figure according to FIG. 2c, which can be ensured by a suitable retaining element not shown. For example, for this purpose, a locking bar pretensioned radially inwards transversely to the longitudinal axis of the ejector tube 19 by means of a spring can be accommodated in a recess in the ejector tube, which locking bar, after the liquid cartridge has passed after the first injection has been triggered, moves radially inwards under the spring pressure, gripping behind the rear edge (in the figure at the right end of the liquid container) of the liquid container and thus preventing it from moving back again. However, it is also possible to pull back the liquid container together with the ejector plunger, optionally also together with the piercing cannula and the outlet nozzle connected to it on the outlet side. In this case, it is advantageous when instead of a thin membrane for closing the liquid container, a rubber plug is provided on its outlet side, which surrounds the piercing cannula with a sufficiently large holding force so that it cannot easily pull itself out of the plug when it is pulled back. The tight fit of the cannula in the stopper plug can be facilitated, for example, by barb elements provided on the outside of the cannula. The ejector plunger 20, which has been pulled back again by momentarily reversing the polarity of the magnetic coil, can be held in its retracted position by means of a small permanent magnet or an electromagnet on the rear cover cap 35 of the housing so that it does not drop again unintentionally and/or prematurely against the shock inducer element (piston 26) on the liquid container solely due to its own weight. The ejector plunger can then, optionally by overcoming the magnetic holding force of the aforementioned (not shown) permanent magnet or electromagnet, be accelerated again to high velocity via the acceleration section lying in front of it, wherein—in case the liquid container remains at the front end of the device—it slides on the end section of its movement with the front pressure piece back into the cylinder space at the rear end of the liquid container and there hits the piston 26 and generates a pressure shock for ejecting a further (small) partial quantity of liquid,—or,—according to the method according to the invention—also accelerates the liquid in the again accelerated container 24 to the initial velocity at which the liquid is then ejected through the cannula and the outlet nozzle without any significant static pressure increase when the liquid container hits the stop element.

The repeated triggering of the electromagnet and the resulting ejection of liquid from the device (after its repositioning at the next, desired injection point) can be done manually, i.e. by actuating a (not shown) triggering mechanism, or automatically at pre-determined time intervals, which can also be very short, for example when using the device as a tattoo machine. An operation of the device with a triggering frequency in the range of 35 to 200 Hz is easily possible with suitable dimensioning of the plunger and the acceleration section.

In FIG. 3, a first preferred embodiment of the outlet nozzle 33 to be used is shown in its mounted state on the housing of the device according to the invention. It can be seen that this outlet nozzle 33 has a central passage 39, running coaxially to the cannula 30, for the liquid 25 to be injected, which passage has on its passage wall 40 at least one screw-shaped or helical fluid channel 41, which extends from the nozzle inlet 42 on the side of the cannula 30 to the nozzle outlet 43, from which the liquid 25 exits for injection. This helical fluid channel 41 causes a swirl or rotational movement to be imposed on the liquid flowing through the outlet nozzle 33 so that the liquid jet 44 is set in rotation around its jet axis 45 when it exits the nozzle and thus impinges on the substrate 46, in the embodiment the skin of a human or animal, as a rotating liquid jet.

The superposition of the translatory movement of the liquid with the rotation imposed on it causes the liquid jet 44 to practically screw or drill itself into the substrate 46 when it impinges on the substrate, wherein the helical movement of the liquid apparently holds the jet together, so that when the liquid impinges on the surface of the skin or substrate, it does not mushroom and splash off sideways, but rather enters the substrate with as little loss as possible and creates an injection channel 47 with a depth T, which depends essentially on the nature of the substrate, the velocity of the liquid jet in the axial direction and its cross-section. In the embodiment shown, the passage 39 in the outlet nozzle has a diameter of approx. 80 to 100 µm on the outlet side and the (first) partial flow flowing through the nozzle passage 39 as a result of the impulse when the liquid container hits the stop exits the nozzle at a velocity in the order of 100 to 1000 m/s. The depth of the resulting injection channel in (human or animal) tissue can thus be adjusted between a few millimetres and a few centimetres.

FIG. 4 shows a further embodiment of an outlet nozzle according to the invention, wherein corresponding features are provided with the same reference signs as for the first embodiment. The outlet nozzle 33 shown in FIG. 4 is fixed to the housing by means of a union nut 34a, which also forms a spacer or depth gauge. The outlet nozzle shown in FIG. 4 can be pressed a little bit into the substrate 46, namely from its upper side 48 into the skin of a patient, so that it forms a trough-like depression 49 therein. A radially outwardly projecting ring area 50 on the union nut 34a limits the depth of depression of the nozzle or indicates when a desired depth has been reached, which is the case when the outer edge of the ring area 50 also comes into contact with the skin surface 48. The outlet nozzle 33 has a passage 39 with an approximately cup-shaped nozzle chamber 51 on the inlet side, on the wall of which two (or more) fluid channels 41 are formed, which wrap around each other helically in the manner of a double (or multiple) helix and which, as described, impose a swirl (spiral movement) on the liquid flowing through the nozzle. The nozzle has two (or also several) laterally e.g. radially outwardly open nozzle outlets 43, through which, in contrast to the first embodiment of the device, jets of liquid 44 do not leave the nozzle coaxially to its longitudinal direction, but in directions which are essentially perpendicular to the longitudinal axis of the device or—in the embodiment shown—even an angle α, which can be slightly greater than 90°. In this way it is easily possible to inject the liquid not perpendicularly to the substrate surface, but to distribute it under the uppermost skin layer 52 essentially parallel to the surface in the substrate.

The embodiment of an outlet nozzle 33 shown in FIG. 5 largely corresponds to that shown in FIG. 3. However, the passage 39 here does not have a constant cross-section over its entire length, but on the inlet side it initially has a converging section 53, whose cross-section decreases in the flow direction 54 of the liquid 25 ejected through the nozzle, and then continues into a section of constant cross-section 55. In both sections 53 and 55, helically spiraling fluid channels 41 are provided on their walls, in the embodiment shown two channels, which are arranged in the manner of a double helix. The converging section firstly ensures an acceleration of the fluid passing from the fluid container into the nozzle.

In the embodiment shown in FIGS. 6 and 7, the outlet nozzle 33 comprises a plurality of orifice plates 58 which are arranged one behind the other in the direction of passage 54 of the liquid in the form of an orifice plate stack 57, which orifice plates each have a slot opening 59 extending over a part of the plate diameter d, the slot openings 59 of successive orifice plates 58 in the orifice plate stack 57 being arranged offset to one another in the circumferential direction by an angular amount B. The amount of this angular offset B in the circumferential direction is smaller at the radially outer ends of the slot openings 59 than the width of the slot openings. This results in a spiral staircase-like fluid channel 41 with a central passage opening. The embodiment with the stacked orifice plates can be manufactured particularly easily and cost-effectively, even having the smallest dimensions with an aperture cross section in the micrometer range.

In the outlet nozzle 33 shown in FIG. 8, four fluid channels 41 are formed on the wall 40 of the passage 39 passing through it, which run in a straight line parallel to the flow direction over the length of the section with constant cross-section 55 and are separated from each other by webs 60. In this embodiment, the entire nozzle is rotatably mounted on the housing of the device and can be driven by an electric motor using a coil. When it is set in rotation during the ejection, the webs on the passage wall transfer this rotational movement to the outer circumferential area of the liquid jet flowing through the nozzle, thus imposing the rotational movement according to the invention on the jet.

The invention provides a method for needleless injection of liquid into a substrate, in particular for injection of a liquid, pharmaceutical or cosmetic product into a biological tissue, wherein liquid is ejected from a fluid supply through an outlet nozzle and exits the nozzle as a fluid jet which enters the substrate, the method being characterized, amongst others, in that a pre-jet is generated by means of a first quantity of liquid exiting the outlet nozzle at high velocity, which pre-jet forms an injection channel in the substrate, and that subsequently at least a second quantity of liquid is passed into the substrate through the injection channel generated by the pre-jet. Preferably the first partial quantity of liquid is ejected through the outlet nozzle under high pressure generated by means of an impulse shock. In an equally advantageous embodiment, at least the pre-jet rotates about its fluid jet axis as it enters the substrate. It may also be provided that at least the first quantity is set in rotation about the fluid jet axis as it passes through the outlet nozzle. The impulse shock is preferably generated by means of an ejector plunger, which is preferably electromagnetically accelerated to an impact velocity and which acts upon at least the first partial quantity of liquid with its mass accelerated to impact velocity. The at least second partial quantity can be ejected through the outlet nozzle by means of the ejector plunger exerting pressure on the liquid. The ejector plunger can be subjected to an electromagnetically generated force to exert pressure on the at least second partial quantity.

The invention further provides an injection device for the needleless injection of a liquid into a substrate, in particular for the injection of liquid pharmaceutical or cosmetic product into a biological tissue, comprising a housing, a liquid supply accommodated or arrangeable in the housing, an outlet nozzle and an ejector device for ejecting liquid from the liquid supply through the outlet nozzle, the injection device being characterized in that the ejector device has means for generating an impulse shock acting on at least a first partial quantity of liquid in the liquid supply, which means of the ejector device for generating the impulse shock can preferably comprise an ejector plunger acceleratable to an impact velocity, with whose mass accelerated to the impact velocity the at least first partial quantity of liquid can be acted upon. The arrangement can preferably be such that the liquid supply can be acted upon by means of an ejector piston which can be actuated by the ejector device and which ejector piston in turn can be acted upon by the ejector plunger or can be formed by the latter. The ejector device may have an electromagnetic drive for the ejector plunger.

The ejector device preferably has an acceleration section for the ejector plunger. The electromagnetic drive may be arranged at a rear end of the housing spaced from the ejector nozzle or approximately in the middle of the housing and the acceleration path may extend between the outlet nozzle and the rear end of the housing.

In a very preferred embodiment, the electromagnetic drive can also have a magnetic coil formed on the ejector plunger itself and, for example, an iron cylinder surrounding the ejector plunger. The ejector plunger can also be provided with an electric power storage device to supply the electromagnet with electric power.

The acceleration section is preferably connected to pressure compensation openings in the area in front of and behind the ejector plunger, wherein these can be connected to each other via an overflow line.

Expediently, the ejector device has means for generating a pressure increase in the liquid supply immediately following the exerted impulse shock, which means for generating the pressure increase can essentially be formed by the ejector plunger which acts on the liquid supply by means of a force-exerting drive after the exertion of the impulse shock. The force-exerting drive can be the electromagnetic drive. In the invention, the liquid supply is preferably contained in a liquid container, which is arrangeable in the housing, preferably replaceable.

The embodiment can also be such that the outlet nozzle is arranged on the liquid container. The outlet nozzle preferably has means to set the fluid jet in rotation, at least in its outer area, before the jet impinges on the substrate. The outlet nozzle may have a nozzle outlet which is substantially coaxial with the housing axis of the housing. However, it is also possible for the outlet nozzle to have a nozzle outlet extending substantially in a plane normal to the housing axis of the housing. The outlet nozzle and/or the front end of the housing can be provided with a depth indicator or a depth stop.

In a particularly advantageous manner, it is possible that the liquid container with the liquid contained therein together with the ejector plunger is movably accommodated in the housing or the acceleration section provided therein and the housing has a stop for the liquid container at its front outlet end. The stop may be provided with a stop damper, for example an elastomeric buffer element.

Finally, the invention also provides a liquid container for use in carrying out the method and/or in the device, which is characterized by at least one piston chamber receiving a first liquid to be injected into a substrate, which piston chamber has a liquid outlet and a shock inducer element for inducing an impulse shock to be exerted on the liquid container.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The invention claimed is:

1. A method for needleless injection of liquid into a substrate, in particular a liquid, pharmaceutical or cosmetic product into a biological tissue, in which the liquid is ejected from a liquid container and through an outlet nozzle and exits this outlet nozzle at a high ejection velocity as a liquid jet which enters the substrate, wherein a plunger and the liquid container together with the liquid contained therein are all continuously accelerated in their entirety from a first position away from the outlet nozzle to an initial velocity and then the liquid container is stopped adjacent to the outlet nozzle, with the continuous acceleration generating sufficient force that the liquid continues to move at a high velocity sufficient to initially eject a first partial quantity of liquid from the container through the outlet nozzle into the substrate, with the plunger thereafter travelling towards the outlet nozzle at a lower velocity to eject a remaining second partial quantity of liquid from the container into the substrate.

2. The method according to claim 1, wherein, before and/or while passing through the outlet nozzle, the liquid jet is set in rotation about its jet axis at least on its outer circumference.

3. An injection device for needleless injection of liquid into a substrate, in particular of a liquid, pharmaceutical or cosmetic product into a biological tissue, comprising a housing for accommodating a liquid container containing the liquid and an ejector device including a plunger for ejecting the liquid from the liquid container through an outlet nozzle, an acceleration device for continuously accelerating the plunger and the liquid container with the liquid contained therein in their entirety from a first position away from the outlet nozzle to an initial velocity inside the housing and a deceleration device adjacent the outlet nozzle for stopping the movement of the liquid container, wherein the acceleration device is configured to generate sufficient force that the liquid continues to move at a sufficient high velocity to eject a first partial quantity of liquid from the container through the outlet nozzle into the substrate, with the plunger thereafter configured to travel towards the outlet nozzle at a lower velocity to eject a remaining second partial quantity of liquid from the container into the substrate.

4. The injection device according to claim 3, wherein the acceleration device comprises a pressure piece arranged on or acting on a rear of the liquid container opposite the outlet nozzle, wherein the pressure piece is acceleratable together with the liquid container and the liquid contained therein in the housing to the initial velocity by means of the ejector device.

5. The injection device according to claim 4, wherein the liquid container has a cylinder space containing the liquid, into which the pressure piece is insertable.

6. The injection device according to claim 5, wherein the liquid container has an acceleration zone which converges from a cross-section of the cylinder space towards an inlet cross-section of the outlet nozzle.

7. The injection device according to claim 3, wherein the deceleration device is substantially formed by a stop acting between the housing and the liquid container.

8. The injection device according to claim 7, wherein the stop is provided with a stop damper.

9. The injection device according to claim 3, wherein the liquid container has a container outlet adapted to an inlet cross-section of the outlet nozzle.

10. The injection device according to claim 3, wherein the liquid container has an outlet side which is closed with a membrane or a pierceable plug which is pierceable by a hollow needle for opening the liquid container.

11. The injection device according to claim 10, wherein the hollow needle is provided on an inlet side of the outlet nozzle.

12. The injection device according to claim 10, wherein the hollow needle is formed in one piece with the outlet nozzle or forms the outlet nozzle itself.

13. The injection device according to claim 3, wherein the outlet nozzle is arranged or arrangeable integrally or replaceably on the liquid container.

14. The injection device according to claim 3, wherein the ejector device has an electromagnetically, chemically and/or gas operated drive.

15. The injection device according to claim 3, wherein the liquid container is replaceably accommodatable in the housing.

16. An injection device for needleless injection of liquid into a substrate, in particular of a liquid, pharmaceutical or cosmetic product into a biological tissue, comprising a housing for accommodating a liquid container containing the liquid and an ejector device including a plunger for ejecting the liquid from the liquid container through an outlet nozzle, an acceleration device for continuously accelerating the plunger and the liquid container with the liquid contained therein in their entirety from a first position away from the outlet nozzle to an initial velocity inside the housing and a deceleration device adjacent the outlet nozzle for stopping the movement of the liquid container, wherein the acceleration device is configured to generate sufficient force that the liquid continues to move at a sufficient high velocity to eject a first partial quantity of liquid from the outlet nozzle into the substrate, with the plunger thereafter configured to travel towards the outlet nozzle at a lower velocity to eject a remaining second partial quantity of liquid from the container into the substrate; and wherein the liquid container has an outlet side which is closed with a membrane or a pierceable plug which is pierceable by a hollow needle for opening the liquid container.

17. The injection device according to claim 16, wherein the hollow needle is provided on an inlet side of the outlet nozzle.

18. The injection device according to claim 16, wherein the hollow needle is formed in one piece with the outlet nozzle or forms the outlet nozzle itself.

* * * * *